US012765793B1

(12) United States Patent
Vitsnudel et al.

(10) Patent No.: US 12,765,793 B1
(45) Date of Patent: Oct. 20, 2026

(54) NON-INVASIVE RADIO FREQUENCY BIOSENSOR

(71) Applicant: AMAZON TECHNOLOGIES, INC., Seattle, WA (US)

(72) Inventors: Ilia Vitsnudel, Even Yehuda (IL); Layne Christopher Price, Seattle, WA (US); Christopher Raymond Grajewski, Sammamish, WA (US); David Heckerman, Bellevue, WA (US); Andreas Caduff, Clyde Hill, WA (US); Adrian Napoles, Bellevue, WA (US); Konstantin Brook, Tel Aviv (IL)

(73) Assignee: Amazon Technologies, Inc., Seattle, WA (US)

(*) Notice: Subject to any disclaimer, the term of this patent is extended or adjusted under 35 U.S.C. 154(b) by 1231 days.

(21) Appl. No.: 17/656,777

(22) Filed: Mar. 28, 2022

(51) Int. Cl.

| | |
|---|---|
| ***A61B 5/05*** | (2021.01) |
| ***A61B 5/00*** | (2006.01) |
| ***A61B 5/024*** | (2006.01) |
| ***A61B 5/145*** | (2006.01) |
| ***H01Q 1/27*** | (2006.01) |

(52) U.S. Cl.
CPC ................ *A61B 5/05* (2013.01); *A61B 5/145* (2013.01); *A61B 5/7203* (2013.01); *A61B 5/7278* (2013.01); *H01Q 1/273* (2013.01); *A61B 5/02416* (2013.01); *A61B 2560/0431* (2013.01)

(58) Field of Classification Search
CPC ......... A61B 5/05; A61B 5/145; A61B 5/7203; A61B 5/7278; A61B 5/02416; A61B 2560/0431; H01Q 1/273
See application file for complete search history.

(56) References Cited

U.S. PATENT DOCUMENTS

2008/0042903 A1* 2/2008 Cheng .................... H01Q 9/065 343/700 MS
2019/0069399 A1 2/2019 Yoshida et al.
2019/0317177 A1 10/2019 Ertan et al.
(Continued)

FOREIGN PATENT DOCUMENTS

CN 214317214 U * 10/2021 ............... A44C 5/24

OTHER PUBLICATIONS

"Body area network", Wikipedia, 6 pages. Retrieved from the Internet on Feb. 23, 2022. URL: https://en.wikipedia.org/wiki/Body_area_network.

*Primary Examiner* — Catherine T. Rastovski
*Assistant Examiner* — Nyla Gavia
(74) *Attorney, Agent, or Firm* — Athorus, PLLC

(57) ABSTRACT

Data about concentration of one or more types of molecules present within a human body are determined noninvasively using radio frequency (RF) signals. RF signals at several different frequencies and at very low power levels are emitted at different times from different antennas of a sensor device. In one implementation, an antenna array comprises five antennas in a quincunx arrangement. The sensor device may also include photoplethysmographs or other sensors. Signals from the sensor device are used to determine compensated data that compensates for motion of the sensor device with respect to the user. This motion may be transient, the result of the user repositioning the sensor device, and so forth. The compensated data may then be used to determine the concentration of one or more types of molecules within the user.

20 Claims, 10 Drawing Sheets

(56) References Cited

U.S. PATENT DOCUMENTS

| | | | | |
|---|---|---|---|---|
| 2019/0356177 | A1* | 11/2019 | Swan | H02J 50/90 |
| 2020/0212985 | A1 | 7/2020 | Lin et al. | |
| 2020/0268266 | A1* | 8/2020 | Majava | A61B 5/02438 |
| 2022/0192510 | A1* | 6/2022 | Leabman | H01Q 1/273 |

* cited by examiner

NON-INVASIVE RADIO FREQUENCY BIOSENSOR

BACKGROUND

Physiological data may be used to help a user manage their health, make more informed decisions, and improve the quality of their life. For example, physiological data such as hydration level, glucose concentration, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
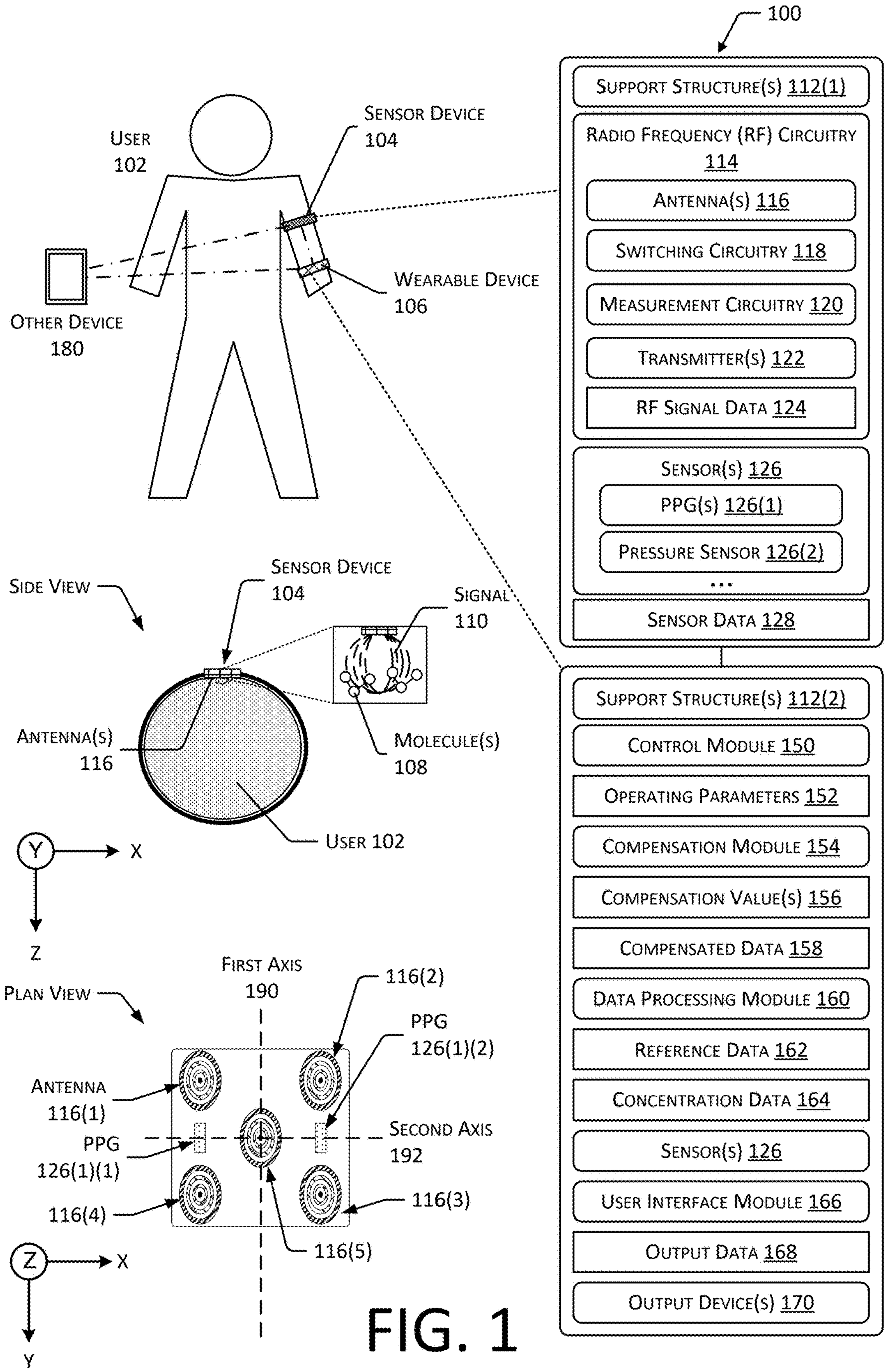
FIG. 1 is an illustrative system that includes a sensor device with an antenna array that uses radio frequency signals to determine molecular concentrations of molecules of interest in a user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

The human body utilizes many different kinds of molecules to function. For example, glucose provides energy for cellular activity while water provides a medium to carry molecules such as glucose and also acts as a reactant. Other molecules may be introduced into the body. For example, alcohol may be consumed, carbon monoxide may be inhaled, a pesticide may be absorbed through the skin, and so forth.

Information about the concentration of one or more types of molecules within the tissues of the body is useful in many situations. For example, a person who is diabetic needs to know the concentration of glucose in their blood in order to keep that concentration in a healthy range. In another example, an athlete needs to make sure they are sufficiently hydrated to maximize their physical performance and avoid injury due to dehydration. Continuing the example, the athlete may also want to monitor their sodium and potassium levels to maintain an optimal level of electrolytes.

Traditionally, information about the concentration of one or more types of molecules has been obtained through invasive measurement of a sample obtained from the person or insertion of a probe into the person. For example, to measure glucose levels a sample of blood is taken and applied to a chemical test strip. In another example, an invasive probe is inserted into the person to measure glucose levels. In another example, a rough estimate of dehydration can be obtained by assessing skin turgor, such as by pinching the skin on the back of the hand. However, traditional methods have significant drawbacks. Obtaining samples of blood or other tissues or insertion of probes into the body requires piercing the skin, injuring the person and introducing a possibility of infection. Additionally, such testing can be costly due to special handling considerations, use of consumables such as reagents, and so forth. Mechanical measurements, such as assessment of skin turgor, lack precision.

Described in this disclosure is a radio frequency (RF) biosensor comprising RF circuitry to acquire data that is then used to non-invasively measures molecular concentration of one or more types of molecules within a user. The RF circuitry includes a transmitter that generates a very low power RF signal that is emitted from one or more antennas in an antenna array, with the electromagnetic field from the antennas impinging upon a portion of the user. The antenna array is maintained proximate to the user, such as with a strap, adhesive, or other mechanism. The presence of different concentrations of molecules will interact with the electromagnetic field from the antenna and introduce changes, such as a change in impedance of the antenna. In one implementation, measurement circuitry may determine changes in impedance of the antenna due to changes in the nearby portion of the user that are within the electromagnetic field from the antenna and provide that as RF signal data.

Many factors may affect the determination of the RF signal data, introducing noise or other artifacts into the resulting signal data. In particular, relative motion between the antenna array and the user can introduce unwanted noise which may obscure a signal of interest. In one implementation, the antenna array may be affixed to or be part of a rigid or semi-rigid structure that is worn on an upper portion of the user's arm. Relative motion, such as transverse tilt of the antenna array with respect to the arm, the antenna array being manually moved by the user or sliding along the upper arm, and so forth changes the interaction between the electromagnetic fields from the respective antennas in the array. These changes introduce variations in amplitude of the overall signal, introduce noise artifacts, and so forth. As a result, recovering the signal of interest that is associated with the type of molecule to be sensed may be difficult.

Described in this disclosure are systems and techniques that substantially improve the performance of a non-invasive radio frequency biosensor. In one implementation, a sensor device may comprise an antenna array. The sensor device may be physically separated from another device, such as a wearable device, smartphone, and so forth. This physical separation may be used to reduce the overall mass and volume of the sensor device. By reducing the overall mass and volume, the sensor device, a strap, adhesive, or other mechanism is able to maintain the antenna array in a desired position with minimal relative movement. For example, a low mass and compact sensor device containing the antenna array is better able to move with the user and conform to changes in surface topology of the skin due to contraction of underlying muscles.

The antenna array comprises a plurality of antennas. Each of the antennas may have a respective ground plane. The antennas in the antenna array may be arranged in various patterns. For example, the antennas may be arranged in an “X” or quincunx pattern, with a central antenna surrounded by peripheral antennas. Based on differences in the signals resulting from the use of different antennas, relative motion such as transverse tilt of the antenna array may be compensated for. For example, if the antenna array is tilted such that the left side is lifted from the skin while the right side is pressed into the skin, the relative amplitude of the signals from the antennas on the left will be decreased relative to the signals from the antennas on the right. These signals are processed to provide RF signal data and may then be used to determine compensation values that are subsequently used to determine compensated data. The compensated data may then be processed to determine concentration data indicative of a concentration of a particular type of molecule within the user.

In some implementations, one or more of the antennas in the antenna array may include a plurality of antenna elements. In this implementation, switching circuitry allows different combinations of antenna elements to be connected to the transmitter. By selectively using particular antenna elements, different electromagnetic field shapes may be produced from a particular antenna. These different field shapes extend different distances from the antenna, allowing information to be obtained about different depths within the user. Similarly, antenna switching circuitry allows different antennas, or the respective elements thereof, to be connected to the transmitter at a specified time. For example, at a first time a first antenna is operated, at a second time a second antenna is operated, and so forth.

The RF circuitry may utilize different frequencies at different times. For example, the transmitter may comprise one or more transmitters to generate signals in different frequency bands, providing RF signal data for the different bands. For example, the first signal may be transmitted at 32 megahertz (MHz), a second signal at 5 gigahertz (GHz), a third signal at 5 kilohertz (KHz), a fourth signal at 100 GHz, and so forth.

The sensor device may also include other sensors. In one implementation, a pair of photoplethysmographs (PPGs) may be arranged within or proximate to the antenna array, one on either side of a long axis of the arm when the sensor device is worn. Sensor data from the PPGs may be used to determine, from the RF signal data, the compensated data, accounting for effects such as a transverse tilt of the sensor device or other movement. For example, amplitude changes in the sensor data from the PPG may be used to adjust the RF signal data, providing the compensated data. In some implementations a single PPG may be used.

The compensation values may be compared to reference data to determine one or more of presence of or concentration of one or more types of molecules present within the user. In one implementation, the compensated data comprising the impedances presented at different frequencies and corrected using the compensation values may be used to determine a concentration of a type of molecule, such as glucose. For example, the molecular concentration data may describe a linear relationship between impedances at particular frequencies and glucose concentration. In other implementations, the concentration of other types of molecules may be determined. For example, the concentration of water may be determined, providing information about a hydration level of the user.

Overall exposure to RF signals is limited, as the output power is extremely low and duration of the RF signals may be very short. For example, the modulation of the signals may be a continuous wave with a total duration of less than 1 millisecond (ms) and with a transmitter output power of 0 decibel-milliwatts (dBm). The sampling frequency, that is how often the RF signals are transmitted to gather data, may also be low, further reducing RF exposure. For example, the system may transmit signals once every six minutes, producing sets of ten samples per hour with each set comprising RF signal data for the various frequency bands.

By using the system described in this disclosure, information about the concentration of various types of molecules at different depths within the user may be determined non-invasively. The ability to quickly and accurately determine the compensated data improves the quality of the measurements acquired, improving the quality of the resulting information such as concentration data. The information provided by the system may be used to help diagnose, treat, or inform the user as to their physiological status. By acting on this information, the overall health of the user may be improved.

Illustrative System

FIG. 1 is an illustrative system 100 that may be used by a user 102, the system comprising a sensor device 104 and may include a wearable device 106 that uses radio frequency (RF) signals to determine molecular concentrations of molecules of interest in at least a portion of the user's body, according to one implementation.

The user 102 may have one or more devices on or about their person, such as the sensor device 104. The sensor device 104 may also be implemented in various physical form factors and is discussed in more detail below including, but not limited to: a wrist band, torc, arm band, ankle band, abdominal strap, and so forth. The wearable device 106 may be implemented in various physical form factors, including but not limited to: wrist bands, torcs, arm bands, ankle bands, abdominal straps, attached to a belt, carried in a pocket, and so forth. In other implementations the device may be implemented in other physical form factors. For example, the components associated with one or more of the sensor device 104 or the wearable device 106 may be incorporated into a tabletop unit, handheld unit, integrated into an operating table, hospital bed, wheelchair, and so forth.

The user's 102 body contains one or more different types of molecules 108. For example, the blood of the user 102 may include glucose, water, creatinine, and so forth. Sometimes the body may include molecules 108 that are exogenous. For example, if the user 102 consumes alcohol, inhales carbon monoxide, absorbs a pesticide through the skin, and so forth, presence or concentration of those types of molecules 108 may be present in the dermis, within the blood, or other tissues within the body. As described below, a radio frequency (RF) signal 110 may be used to determine information about one or more molecules 108.

The sensor device 104 may include at least one support structure 112(1) that supports one or more of the following components. The support structure 112(1) may comprise one or more of a strap, sleeve, elastomeric sheath, adhesive, and so forth. For example, the sensor device 104 may comprise a housing or capsule that is attached to a band, allowing the sensor device 104 to be retained on the upper arm of the user 102 as shown in FIG. 1. In another example, the sensor device 104, or a portion thereof, may comprise an adhesive patch to adhere to the user 102 during operation. Also shown in FIG. 1 is a side view of the sensor device 104 as shown worn on the upper arm. An enlarged view shows the signal 110 and the molecules 108 in the upper arm.

The sensor device 106 includes radio frequency (RF) circuitry 114 that includes one or more antennas 116, switching circuitry 118, measurement circuitry 120, one or more transmitters 122, and may include other circuitry. Each antenna 116 may comprise one or more antenna elements in particular arrangements. For example, the antenna elements may comprise a first antenna element and one or more additional antenna elements that are arranged around the first antenna element. The overall arrangement of an individual antenna 116 may appear as an elongated oval, with a long axis extending through a long axis of the elongated oval. In some implementations, during use the long axis of the antenna 116 may be arranged to parallel a long axis of a limb such as an arm or leg of the user 102.

A plurality of antennas 116 of the sensor device 104 may be used to provide an antenna array, such as shown here in a plan view. In this implementation, the sensor device 104 is shown in a plan view, with the antenna array comprising five antennas 116(1), 116(2), 116(3), 116(4), and 116(5) that are arranged in an "X" or quincunx pattern. Antenna 116(5) is in the center of the antenna array while the other antennas 116 are arranged at the relative corners of a square. In the implementation shown, the antenna array has an overall square shape, with a first axis 190 and a second axis 192 perpendicular to the first axis 190. While being worn by the user 102, the first axis 190 may be parallel to a long axis of the arm of the user 102. In other implementations, the antenna array may use other arrangements, such as three antennas centered along the second axis, a hexagonal arrangement with an antenna at each vertex and one in the center, and so forth. Also shown within the antenna array of the sensor device 104 are two photoplethysmographs (PPGs) 126(1), a first PPG 126(1)(1) to the left of the first axis 190 and a second PPG 126(1)(2) to the right of the first axis 190. Operation of the antenna array and other sensors such as the PPGs 126 is discussed in more detail in the following.

The switching circuitry 118 selectively couples the output from the transmitter(s) 122, via the measurement circuitry 120, to one or more of the antennas 116 or their respective antenna elements. For example, at a first time the switching circuitry 118 may couple the transmitter 122 and measurement circuitry 120 to the first antenna 116(1), at a second time couple the transmitter 122 to the second antenna 116(2), and so forth.

The transmitter 122 is configured to generate an RF signal 110. The transmitter 122 may be able to generate RF signals 110 at one or more frequencies, in one or more frequency bands or ranges, and so forth. For example, the transmitter 122 may be able to generate RF signals 110 at one or more of the 1 kHz, 32 MHz, 5 GHz, or other bands. The RF signal 110 that is generated may be modulated with a continuous wave.

During operation to determine a measurement associated with the user 102, the transmitter 122 provides the RF signal 110 to the measurement circuitry 120 that in turn provides the RF signal 110 to the switching circuitry 118. The switching circuitry 118 then directs the RF signal 110 to a set of the one or more of the antennas 116 or the antenna elements of an individual antenna 116. For example, output from the transmitter 122 may be connected to a first antenna element in the antenna 116 at a first time. The antenna 116 emits the signal 110 which then impinges on the body of the user 102 while the wearable device 106 is being worn or held close to the user 102. At a second time, a second set of the one or more antenna elements of the antenna 116 may be used.

The measurement circuitry 120 determines RF signal data 124 associated with one or more of the operation of the transmitter 122, the load presented by the antenna 116, and so forth. The RF signal data 124 may include information such as frequency data indicative of the frequency of the generated signal 110, impedance data indicative of impedance presented by the antenna 116 comprising the set of antenna elements connected via the switching circuitry 118, amplitude data indicative of an amplitude of the RF signal 110, and so forth. For example, the measurement circuitry 120 may determine an impedance presented by the antenna 116 to the first signal 110 at 32 MHz. The measurement circuitry 120 may comprise a vector voltmeter or other device that measures the voltage of the signal 110. In some implementations, the RF signal data 124 may comprise discrete sets of data, each set associated with a respective antenna 116 in the antenna array, frequency, and so forth. For example, the RF signal data 124 may comprise first RF signal data 124(1) acquired using the first antenna 116(1) at 32 MHz, second RF signal data 124(2) acquired using the second antenna 116(2) at 32 MHz, third RF signal data 124(3) acquired using the third antenna 116(3) at 32 MHz, and so forth. The RF signal data 124 may comprise a time series of one or more characteristics, such as impedance, amplitude, phase, frequency, and so forth.

While a transmitter 122 is shown, it is understood that in other implementations the RF circuitry 114 may include a plurality of transmitters, digital synthesizers, or other components such as receiver, transceiver, and so forth.

The use of the sensor device 104 that provides a relatively low mass and small volume may improve the quality of data obtained by minimizing variations in output of the RF signal data 124 due to motion of the user 102. For example, the more compact and lighter sensor device 104 may be easier to maintain in a fixed relative position with respect to the user 102 while the user 102 moves. Other techniques may also be used to process the RF signal data 124 to produce compensated data 158, as described below.

In addition to the RF circuitry 114, the sensor device 104 may include other sensors 126 that determine sensor data 128. The sensors 126 may include one or more photoplethysmographs (PPGs) 126(1) as described above, one or more pressure sensors 126(2) to determine pressure sensor data indicative of mechanical pressure of the sensor device 104 with respect to the user 102, and so forth. The sensors 126 are discussed in more detail with respect to FIG. 2.

The sensor device 104 may be in communication with the wearable device 106. In one implementation, the sensor device 104 may be connected to the wearable device 106 via one or more electrical conductors, waveguides, coaxial cables, optical fibers, and so forth. In another implementation, the sensor device 104 may communicate wirelessly with the wearable device 106, or an other device 180 such as a tablet, smartphone, laptop, access point, and so forth. For example, the sensor device 104 and the wearable device 106 may communicate using Bluetooth, WiFi, a body area network (BAN), and so forth.

The wearable device 106 may include at least one support structure 112(2) that supports one or more of the following components. For example, the wearable device 106 may comprise a housing or capsule that is attached to a wrist band, allowing the wearable device 106 to be retained on the wrist of the user 102 as shown in FIG. 1. In another example, the wearable device 106, or a portion thereof, may comprise an adhesive patch to adhere to the user 102 during operation. In yet another example, the wearable device 106 may be carried in a pocket, pouch, sling, and so forth.

A control module 150 may be used to direct operation of the RF circuitry 114 or other components such as the sensors 126. For example, the control module 150 may comprise a hardware processor (processor) executing instructions that operate the measurement circuitry 120 to operate the switching circuitry 118 to connect a particular antenna 116 or set of antenna elements of the antenna 116 to the transmitter 122, operate the transmitter 122 to transmit particular signals 110 at particular frequencies at particular times, acquire RF signal data 124 during operation of the transmitter 122, and so forth. In another example, the control module 150 may operate the PPGs 126(1) at a specified time interval to provide sensor data 128.

The control module 150 may use one or more operating parameters 152 to control operation. The operating parameters 152 may specify one or more of frequency, output power, modulation, signal duration, operating sequence of antennas 116 in the antenna array, particular antenna elements for each antenna 116 to be used to emit the signal 110, and so forth. For example, the operating parameters 152 may specify that a signal 110 is to be transmitted with a center frequency of 32 MHz at 0 dBm, continuous wave (CW) modulation, particular sets of antenna elements to use to obtain data from the desired depths, and so forth. In another example, the operating parameters 152 may specify that the compensation values 156 are to be determined before every nth operation, where n is a non-zero positive integer.

The operating parameters 152 may specify a sample depth and associated configuration on antenna elements. For example, a "shallow" sample depth may correspond to an antenna configuration or set of antenna elements in which the first antenna element is connected to the transmitter 122 and used to emit the signal 110. In comparison, a "deep" sample depth may correspond to an antenna configuration or set of antenna elements in which the first antenna element, a second antenna element, and a third antenna element are simultaneously connected to the transmitter 122 and used to emit the signal 110.

Once the operating parameters 152 have been determined, the control module 150 or another component may operate the circuitry in the sensor device 104, the wearable device 106, or both. For example, the control module 150 may operate the RF circuitry 114 at a first time to selectively connect the antennas 116 in the antenna array to the transmitter 122, operate the transmitter 122 to generate a first signal 110 at a first frequency, and operate the measurement circuitry 120 to determine RF signal data 124 representative of impedance values.

As the RF signals 110 emitted by the antenna 116 impinge on the body of the user 102, they are affected by the molecules 108 therein. Various interactions take place between the signals 110 and the molecules 108. For example, the presence of glucose in the body within the volume encompassed by the electromagnetic field produced by the antenna 116 during operation of the transmitter 122 may result in a change in impedance that the antenna 116 that is connected via the switching circuitry 118 presents to the transmitter 122. As described below, a presence or concentration of a type of molecule 108 may be determined based on one or more of the impedance or other characteristics such as frequency, phase, and so forth that are expressed in the RF signal data 124.

A compensation module 154 accepts the RF signal data 124 as input and may also accept sensor data 128 from other sensors, such as one or more PPGs 126(1) in some implementations. The compensation module 154 may determine one or more compensation values 156. The compensation module 154 may process at least a portion of the RF signal data 124 using the one or more compensation values 156 to determine compensated data 158.

In one implementation, the RF signal data 124 associated with different antennas 116 of the antenna array may be processed to determine a relative compensation. For example, if the sensor device 104 and the antenna array therein experience a transverse tilt relative to the arm of the user 102. As a result, the RF signal data 124 from antennas 116(1) and (4) that are pressed into the arm may exhibit greater amplitudes than the RF signal data 124 from antennas 116(2) and 116(3) that are pulled away from the arm, with the RF signal data 124 from a central antenna 116(5) having an amplitude between. Based on this relative variance in amplitude, the compensation module 154 may determine the compensation values 156. In one implementation, based on the relative variation in signal amplitudes, the compensation value(s) 156 may be retrieved from a lookup table or other data structure. The compensation values 156 may then be used to scale, amplify, attenuate, or otherwise modify the values of the RF signal data 124 to determine the compensated data 158. The compensation module 154 may operate to normalize the RF signal data 124 to determine the compensated data 158.

In another implementation, the RF signal data 124 may be provided as input to a trained machine learning system, such as a trained neural network. In this implementation, the compensation values 156 may comprise weights of the nodes within the machine learning system. The trained machine learning system may accept the RF signal data 124 as input and determines as output the compensated data 158.

The compensated data 158 is representative of the RF signal data 124, but with noise and artifacts resulting from relative movement between the antenna array and the user 102 being substantially reduced or eliminated. As a result, the operation of the subsequent data processing module 160 to determine concentration data 164 is improved.

The compensation module 154 may use other sensor data 128 in addition to, or instead of, the RF signal data 124 to determine the compensated data 158. In one implementation one or more PPGs 126(1) may provide sensor data 128. The sensor data 128 may comprise a time series of measurements acquired by the PPG 126(1). A PPG 126(1) may operate by using a light source or emitter to illuminate a portion of the user 102 and a detector to receive the reflected light. The detector will thus provide information, such as a varying amplitude of received light, that varies responsive to changes in underlying blood volume resulting from a cardiac pulse or other effect.

The compensation module 154 may use the sensor data 128 from one or more PPGs 126(1) as, or to determine, the compensation values 156. A PPG 126(1) is also sensitive to movement artifacts due to relative motion of the user 102 with respect to the PPG 126. However, while the RF circuitry 114 provides information about some types of molecules 108, the PPG 126(1) is sensitive to others. For example, the RF circuitry 114 may be designed to provide information about glucose, while the PPG 126(1) is sensitive to hemoglobin. Due to the difference in operation, the difference in types of molecule 108 being sensed, and so forth, the PPGs 126(1) provide a useful signal to detect relative motion.

In one implementation, the sensor data 128 from a PPG 126(1) is acquired during the same time as RF signal data 124. The sample rates of the respective data may differ, but there is a common time window during which information is acquired from both the RF circuitry 114 and the PPG 126(1). The RF circuitry 114 may be operated synchronously or asynchronously with respect to the sensors 126 such as the PPG 126(1).

In this implementation, the compensation module 154 scales the sensor data 128, with the scaling provided by a linear regression of the RF signal data 124. The resulting compensation values 156, comprising the scaled sensor data 128, are then subtracted from amplitude values of samples in the RF signal data 124 at the same or proximate time. The results of this technique are depicted and discussed with regard to FIG. 9.

In other implementations, other signal processing techniques may be used to determine the compensation values 156 based on the sensor data 128. In other implementations other sensors 126 may be used instead of, or in addition to the PPGs 126(1). For example, the sensor device 104 may include one or more pressure sensors 126(2). Based on the sensor data 128 comprising pressure sensor data provided by the pressure sensors 126(2), the compensation module 154 may determine the compensation values 156 and the compensated data 158.

A data processing module 160 may use at least the compensated data 158 as input. The data processing module 160 may also access reference data 162. The reference data 162 comprises information that, for a particular type of molecule 108, associates one or more compensated data 158 with information such as concentration of the particular type of molecule 108. The reference data 162 may be general or specific to a particular user 102. For example, the reference data 162 may be generated and associated with particular user 102(1) "Pat".

The data processing module 160 may use the compensated data 158 and the reference data 162 to determine molecular concentration data 164. The molecular concentration data 164 may specify a mass per unit volume. For example, the compensated data 158 may indicate the impedance value at 32 MHz is 51.7 ohms. This value may be used as input to the reference data 162 which corresponds to molecular concentration data 164 indicative of a mass per volume, such as a glucose concentration of 159 milligrams per deciliter (mg/dL).

The RF signal data 124 used to determine the compensated data 158 may be obtained for a plurality of different frequencies and may be obtained using a variety of different antennas 116 and sets of antenna elements of the antenna 116 to emit the signals 110. The compensated data 158 may be used to determine the molecular concentration data 164 for one or more different types of molecules 108. For example, the molecular concentration data 164 may indicate the concentration of glucose and water in the body of the user 102.

The wearable device 106 may include, or receive data from, one or more other sensors 126. For example, a temperature sensor may be used to provide an indication of the body temperature of the user 102. The body temperature may then be used as an input to the data processing module 160 to improve the accuracy of the molecular concentration data 164. These sensors 126 are discussed in more detail below with regard to FIG. 2. In other implementations, data from the sensors 126 may be obtained to provide other information about physiological status, activity level, and so forth.

Output from the sensors 126 may also be used to determine operation of the data processing module 160. For example, the sensors 126 may include one or more accelerometers. If the accelerometers detect motion that exceeds a threshold value, the data processing module 160 may be operated to determine molecular concentration data 164. For example, if the user 102 has been running, the system 100 may operate to determine glucose concentration. In another example, if the motion of the user 102 is less than a threshold value, the data processing module 160 may be operated to determine molecular concentration data 164. For example, if no movement has been detected for 2 minutes, such as if the user 102 is asleep or unconscious, the data processing module 160 may be operated to determine molecular concentration data 164.

A user interface module 166 may be configured to use the molecular concentration data 164 and produce output data 168. For example, based on the molecular concentration data 164 indicating that the blood glucose level is below a threshold value, output data 168 may be generated. One or more output devices 170 may be used to present a user interface based on at least a portion of the output data 168. Continuing the example, the user interface module 166 may produce output data 168 that comprises instructions to operate a speaker to present an audible prompt indicating the low blood glucose level. In another example, the output data 168 may be provided to the other device 180. For example, the wearable device 106 may be connected via Bluetooth or another wireless protocol to a smartphone, wireless access point, in vehicle computer system, or other device. Based on the output data 168 the other device 180 may present an output to the user 102, alert someone else, modify operation of another device, and so forth. For example, if the wearable device 106 provides data to a vehicle that indicates the user 102 in the driver's seat has a concentration of alcohol that exceeds a threshold value, the vehicle may be prevented from moving, or may only be able to operate in a fully autonomous mode.

FIG. 1 depicts one implementation with regard to the placement of components in the sensor device 104 and the wearable device 106. In other implementations, other arrangements may be used. For example, the sensor device 104 may comprise the antennas 116(1), . . . , 116(N) and the switching circuitry 118 while the wearable device 106 comprises the transmitter(s) 122, measurement circuitry 120, and so forth.

Figure 2:
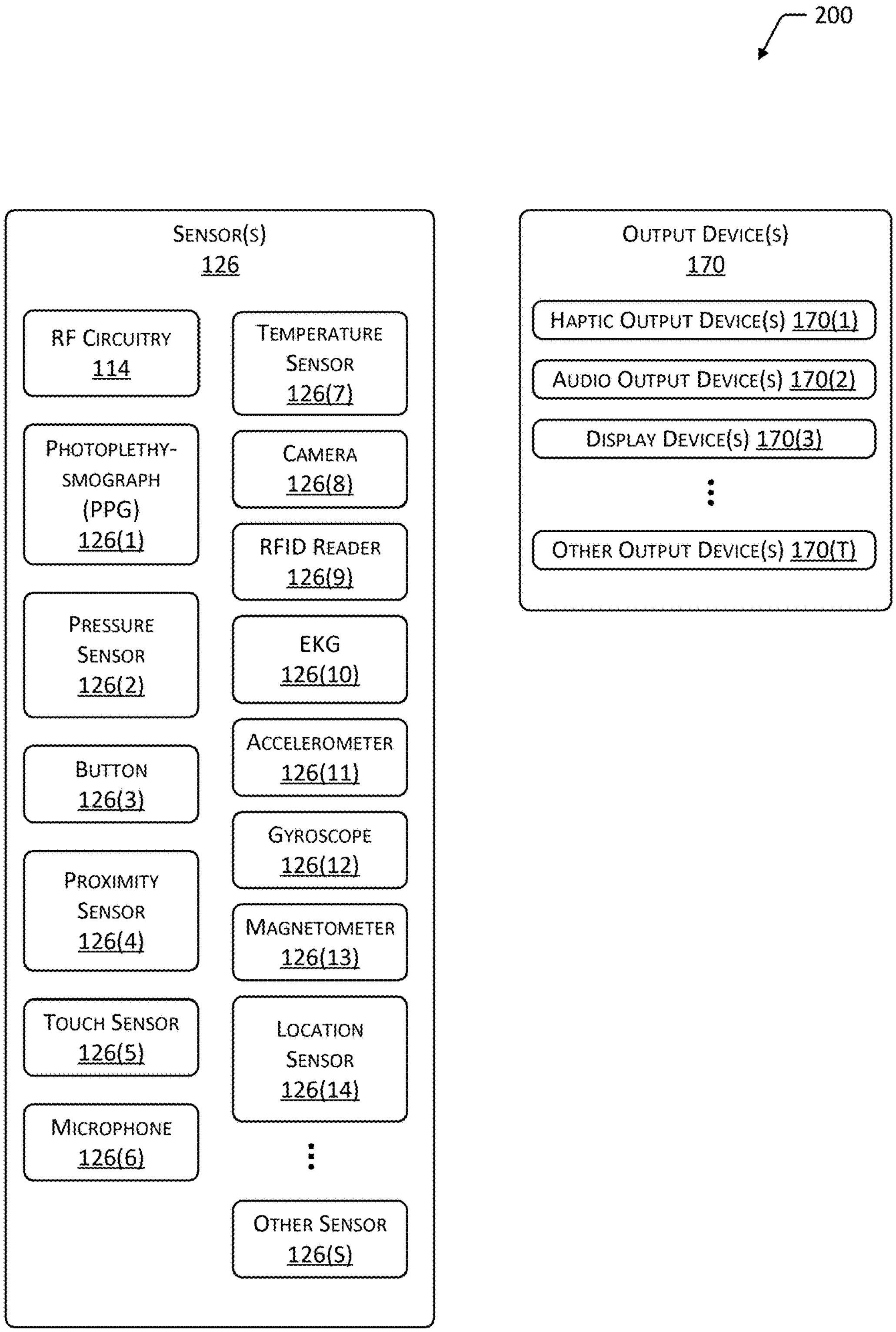
FIG. 2 illustrates a block diagram of sensors and output devices that may be used by the system during operation, according to one implementation.

FIG. 2 illustrates a block diagram 200 of sensors 126 and output devices 170 that may be used by the devices of the system 100 during operation, such as the sensor device 104 or the wearable device 106.

The one or more sensors 126 may be integrated with or internal to the sensor device 104, wearable device 106, or the other device 180. For example, the sensors 126 may be built-in to the sensor device 104 or the wearable device 106 during manufacture. In other implementations, the sensors 126 may be part of another device which is in communication with the sensor device 104 or the wearable device 106. For example, the sensors 126 may comprise a device external to, but in communication with, the wearable device 106 using Bluetooth, Wi-Fi, 4G, 5G, LTE, ZigBee, Z-Wave, or another wireless or wired communication technology.

The sensors 126 may include the RF circuitry 114.

A photoplethysmograph (PPG) 126(1) or pulse oximeter may be configured to provide sensor data 128 that is indicative of a cardiac pulse rate, data indicative of oxygen saturation of the user's 102 blood, and so forth. For example, the photoplethysmograph 126(1) may use an optical emitter such as one or more light emitting diodes (LEDs) and a corresponding optical detector such as a photodetector to perform photoplethysmography, determine cardiac pulse, determine changes in apparent color of the blood of the user 102 resulting from oxygen binding with hemoglobin in the blood, and so forth.

A pressure sensor 126(2) may provide information about the pressure between a portion of the sensor device 104 and a portion of the user 102. For example, the pressure sensor 126(2) may comprise a capacitive element, strain gauge, spring-biased contact switch, force sensitive resistor, or other device that is used to determine the amount of pressure between the user's 102 arm and an inner surface of the sensor device 104 that is in contact with the arm. In some implementations, the pressure sensor 126(2) may provide information indicative of a force measurement, such as 0.5 Newtons, a relative force measurement, or whether the pressure is greater than a threshold value.

In some implementations, operation of one or more components in the sensor device 104 may be based at least in part on information from the pressure sensor 126(2). For example, based on data provided by the pressure sensor 126(2) a determination may be made as to whether at least a portion of the sensor device 104 is in contact with the user 102 or another object. Continuing the example, if the pressure indicated by the pressure sensor 126(2) exceeds a threshold value, the sensor device 104 may be determined to be in contact with the user 102. Based on this determination that the sensor device 104 is in contact with the user 102, one or more of the transmitter 122, receiver, sensors 126, and so forth may be operated. Likewise, data from the pressure sensor 126(2) may be used to determine the sensor device 104 is not in sufficient physical contact with the user 102. As a result, one or more of the transmitter 122, receiver, sensors 126, and so forth may be turned off.

The one or more sensors 126 may include one or more buttons 126(3) that are configured to accept input from the user 102. The buttons 126(3) may comprise mechanical, capacitive, optical, or other mechanisms. For example, the buttons 126(3) may comprise mechanical switches configured to accept an applied force from a touch of the user 102 to generate an input signal.

A proximity sensor 126(4) may be configured to provide sensor data 128 indicative of one or more of a presence or absence of an object, a distance to the object, or characteristics of the object. The proximity sensor 126(4) may use optical, electrical, ultrasonic, electromagnetic, or other techniques to determine a presence of an object. For example, the proximity sensor 126(4) may comprise a capacitive proximity sensor configured to provide an electrical field and determine a change in electrical capacitance due to presence or absence of an object within the electrical field.

The sensors 126 may include one or more touch sensors 126(5). The touch sensors 126(5) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 126(6) may be configured to acquire information about sound present in the environment. In some implementations, arrays of microphones 126(6) may be used. These arrays may implement beamforming techniques to provide for directionality of gain. The one or more microphones 126(6) may be used to acquire audio data, such as speech from the user 102.

A temperature sensor (or thermometer) 126(7) may provide information indicative of a temperature of an object. The temperature sensor 126(7) may be configured to measure ambient air temperature proximate to the user 102, the body temperature of the user 102, and so forth. The temperature sensor 126(7) may comprise a silicon bandgap temperature sensor, thermistor, thermocouple, or other device. In some implementations, the temperature sensor 126(7) may comprise an infrared detector configured to determine temperature using thermal radiation.

The sensors 126 may include one or more cameras 126(8). The cameras 126(8) may comprise a charge coupled device, complementary metal oxide semiconductor, or other image sensor that is able to acquire images.

One or more radio frequency identification (RFID) readers 126(9), near field communication (NFC) systems, and so forth, may also be included as sensors 126. The user 102, objects around a computing device, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise an RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 126 may include an electrocardiograph (EKG) 126(10) that is configured to detect electrical signals produced by the heart of the user 102.

The sensors 126 may include one or more accelerometers 126(11). The accelerometers 126(11) may provide information such as the direction and magnitude of an imposed acceleration. Data such as rate of acceleration, determination of changes in direction, speed, and so forth, may be determined using the accelerometers 126(11).

A gyroscope 126(12) provides information indicative of rotation of an object affixed thereto. For example, the gyroscope 126(12) may indicate whether the device has been rotated.

A magnetometer 126(13) may be used to determine an orientation by measuring ambient magnetic fields, such as the terrestrial magnetic field. For example, output from the magnetometer 126(13) may be used to determine whether the device containing the sensor 126, such as a computing device, has changed orientation or otherwise moved. In other implementations, the magnetometer 126(13) may be configured to detect magnetic fields generated by another device.

A location sensor 126(14) is configured to provide information indicative of a location. The location may be relative or absolute. For example, a relative location may indicate “kitchen”, “bedroom”, “conference room”, and so forth. In comparison, an absolute location is expressed relative to a reference point or datum, such as a street address, geolocation comprising coordinates indicative of latitude and longitude, grid square, and so forth. The location sensor 126 (14) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 126(14) may be omitted or operate in conjunction with an external resource such as a cellular network operator providing location information, or Bluetooth beacons.

The sensors 126 may include other sensors 126(S) as well. For example, the other sensors 126(S) may include strain gauges, anti-tamper indicators, and so forth. For example, strain gauges or strain sensors may be embedded within the sensor device 104 and may be configured to provide information indicating that at least a portion of the sensor device 104 has been stretched or displaced such that the sensor device 104 may have been donned or doffed.

In some implementations, the sensors 126 may include hardware processors, memory, and other elements configured to perform various functions. Furthermore, the sensors 126 may be configured to communicate by way of a network or may couple directly with the computing device.

The sensor device 104, wearable device 106, or other computing device may include or may couple to one or more output devices 170. The output devices 170 are configured to generate signals which may be perceived by the user 102, detectable by the sensors 126, or a combination thereof.

Haptic output devices 170(1) are configured to provide a signal, which results in a tactile sensation to the user 102. The haptic output devices 170(1) may use one or more mechanisms such as electrical stimulation or mechanical displacement to provide the signal. For example, the haptic output devices 170(1) may be configured to generate a modulated electrical signal, which produces an apparent tactile sensation in one or more fingers of the user 102. In another example, the haptic output devices 170(1) may comprise piezoelectric or rotary motor devices configured to provide a vibration that may be felt by the user 102.

One or more audio output devices 170(2) are configured to provide acoustic output. The acoustic output includes one or more of infrasonic sound, audible sound, or ultrasonic sound. The audio output devices 170(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 170(2).

The display devices 170(3) may be configured to provide output that may be seen by the user 102 or detected by a light-sensitive detector such as an image sensor or light sensor. The output may be monochrome or color. The display devices 170(3) may be emissive, reflective, or both. An emissive display device 170(3), such as using light emitting diodes (LEDs), is configured to emit light during operation. In comparison, a reflective display device 170(3), such as using an electrophoretic element, relies on ambient light to present an image. Backlights or front lights may be used to illuminate non-emissive display devices 170(3) to provide visibility of the output in conditions where the ambient light levels are low.

The display mechanisms of display devices 170(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 170(3) may operate as panels, projectors, and so forth.

The display devices 170(3) may be configured to present images. For example, the display devices 170(3) may comprise a pixel-addressable display. The image may comprise at least a two-dimensional array of pixels or a vector representation of a two-dimensional image.

In some implementations, the display devices 170(3) may be configured to provide non-image data, such as text or numeric characters, colors, and so forth. For example, a segmented electrophoretic display device, segmented LED, and so forth, may be used to present information such as letters or numbers. The display devices 170(3) may also be configurable to vary the color of the segment, such as using multicolor LED segments.

Other output devices 170(T) may also be present. For example, the other output devices 170(T) may include scent/odor dispensers.

Figure 3:
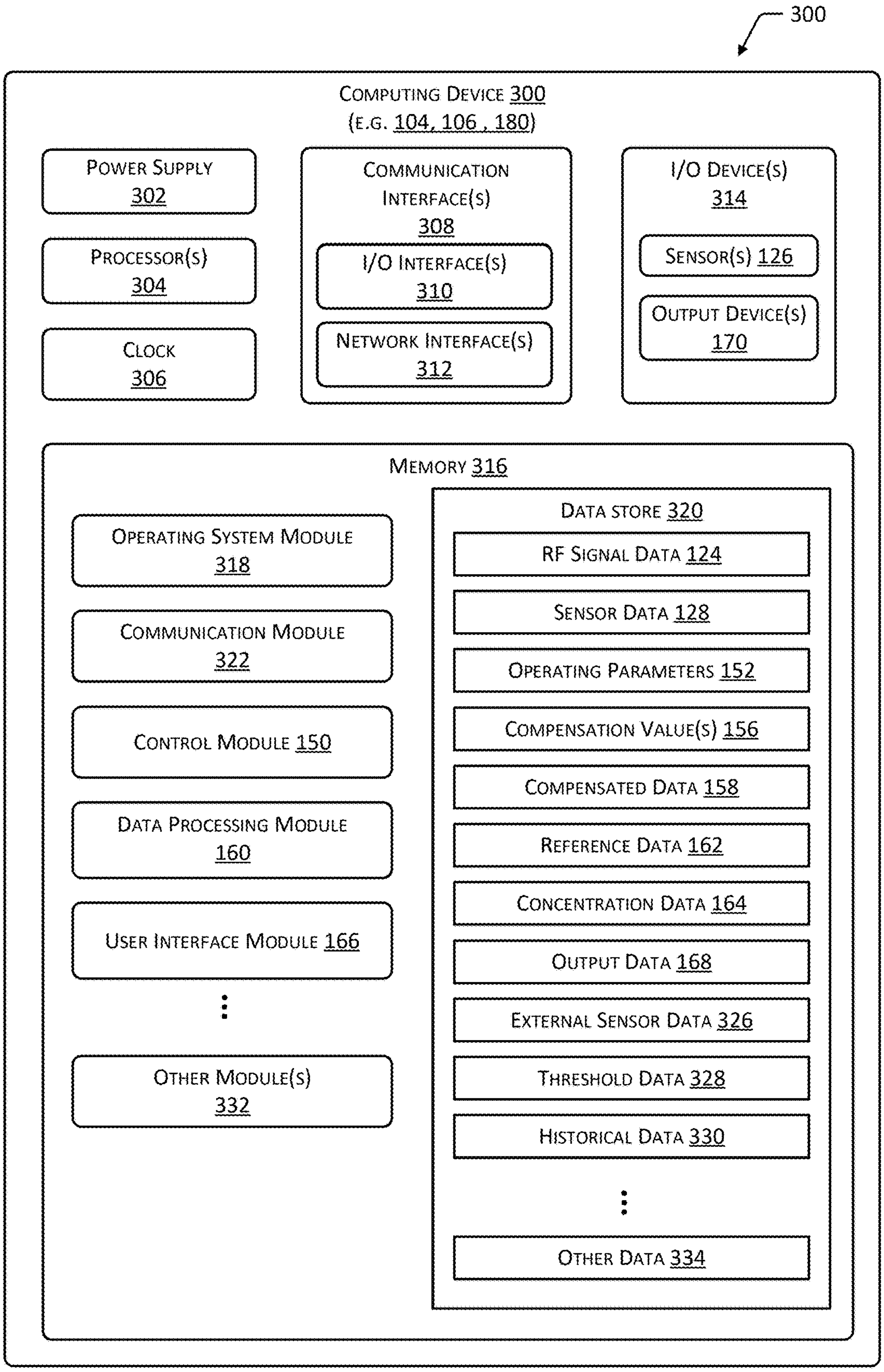
FIG. 3 illustrates a block diagram of a computing device(s) that may be included in or in communication with the sensor device, according to one implementation.

FIG. 3 illustrates a block diagram of a computing device 300 configured to support operation of the system 100. As described above, the computing device 300 may be the sensor device 104, the wearable device 106, the other device 180, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The i/O devices 314 may include input devices such as one or more of a camera 126(8), a sensor 126, keyboard, mouse, scanner, and so forth. The I/O devices 314 may also include output devices 170 such as one or more of a display device 170(3), printer, audio output device 170(2), and so forth. In some embodiments, the I/O devices 314 may be physically incorporated with the computing device 300 or may be externally placed.

The network interfaces 312 are configured to provide communications between the computing device 300 and other devices, such as the sensors 126, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Washington, USA; the Android operating system from Google Corporation of Mountain View, California, USA; the iOS operating system from Apple Corporation of Cupertino, California, USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including other computing devices 300, network attached storage devices, and so forth.

A communication module 322 may be configured to establish communications with one or more of other computing devices 300, the sensors 126, or other devices 180. The communications may be authenticated, encrypted, and so forth. The communication module 322 may also control the communication interfaces 308.

One or more of the RF signal data 124, sensor data 128, the operating parameters 152, compensation values 156, compensated data 158, reference data 162, the concentration data 164, the output data 168, and so forth may be stored in the memory 316.

The memory 316 may also store the control module 150. As described above, the control module 150 may operate the RF circuitry 114 to produce RF signal data 124.

The memory 316 may store the data processing module 160. The data processing module 160 uses the compensated data 158, the reference data 162, and so forth as input to generate the molecular concentration data 164. In some implementations, the molecular concentration data 164 may be indicative of a concentration of one or more types of molecules 108 in the user 102.

In some implementations, a calibration process may be performed in which an external sensor is used to obtain external sensor data 326 that is indicative of a concentration of a type of molecule 108. For example, a blood glucose meter that uses a sample of a drop of blood may be used as the external sensor. At a contemporaneous time, the RF circuitry 114 may be used to obtain the RF signal data 124. The external sensor data 326 comprising concentration data from the external sensor may be used in conjunction with the RF signal data 124 to determine a correspondence between one or more RF signal data 124 and molecular concentration. This correspondence may be stored as the reference data 162. The reference data 162 may be specific to a particular user 102. For example, the reference data 162 may be specific to user 102 "Pat". In some implementations, the reference data 162 may be processed using one or more techniques to interpolate values between those which have been measured. In some implementations, previously acquired reference data 162 may be used, and a calibration factor may be determined based on the reference data 162.

Threshold data 328 may be stored in the memory 316. The threshold data 328 may be used to designate a threshold to which molecular concentration data 164 may be compared. For example, the threshold data 328 may specify threshold values for particular types of molecules 108. If the molecular concentration data 164 is less than a first threshold or greater than a second threshold, the user interface module 166 may generate an alarm and present that information using the output device 170.

The user interface module 166 provides a user interface using one or more of the I/O devices 314. The user interface module 166 may be used to obtain input from the user 102, present information to the user 102, and so forth. For example, the user interface module 166 may present a graphical user interface on the display device 170(3) and accept user input using the touch sensor 126(5).

Continuing the earlier example, if the molecular concentration data 164 indicates that user's 102 blood glucose level is less than a threshold value, the user interface module 166 may present information indicative of this on the display device 170(3). The user 102 may then take corrective actions, such as consuming glucose to raise their blood sugar level, reducing activity, and so forth.

The computing device 300 may maintain historical data 330. For example, the historical data 330 may comprise the RF signal data 124, molecular concentration data 164, or data from one or more of the sensors 126 obtained at different times. The historical data 330 may be used to provide information about trends or changes over time. For example, the historical data 330 may comprise an indication of average daily blood glucose levels of the user 102 over a span of several weeks. The user 102 may then use this data to assist in managing their diet and insulin dosage.

Other modules 332 may also be present in the memory 316, as well as other data 334 in the data store 320.

In different implementations, different computing devices 300 may have different capabilities or capacities. For example, the wearable device 106 may have significantly more processor 304 capability and memory 316 capacity compared to the sensor device 104. In one implementation, the sensor device 104 may determine the RF signal data 124 and send that date to the other device 180. Other combinations of distribution of data processing and functionality may be used in other implementations.

Figure 4:
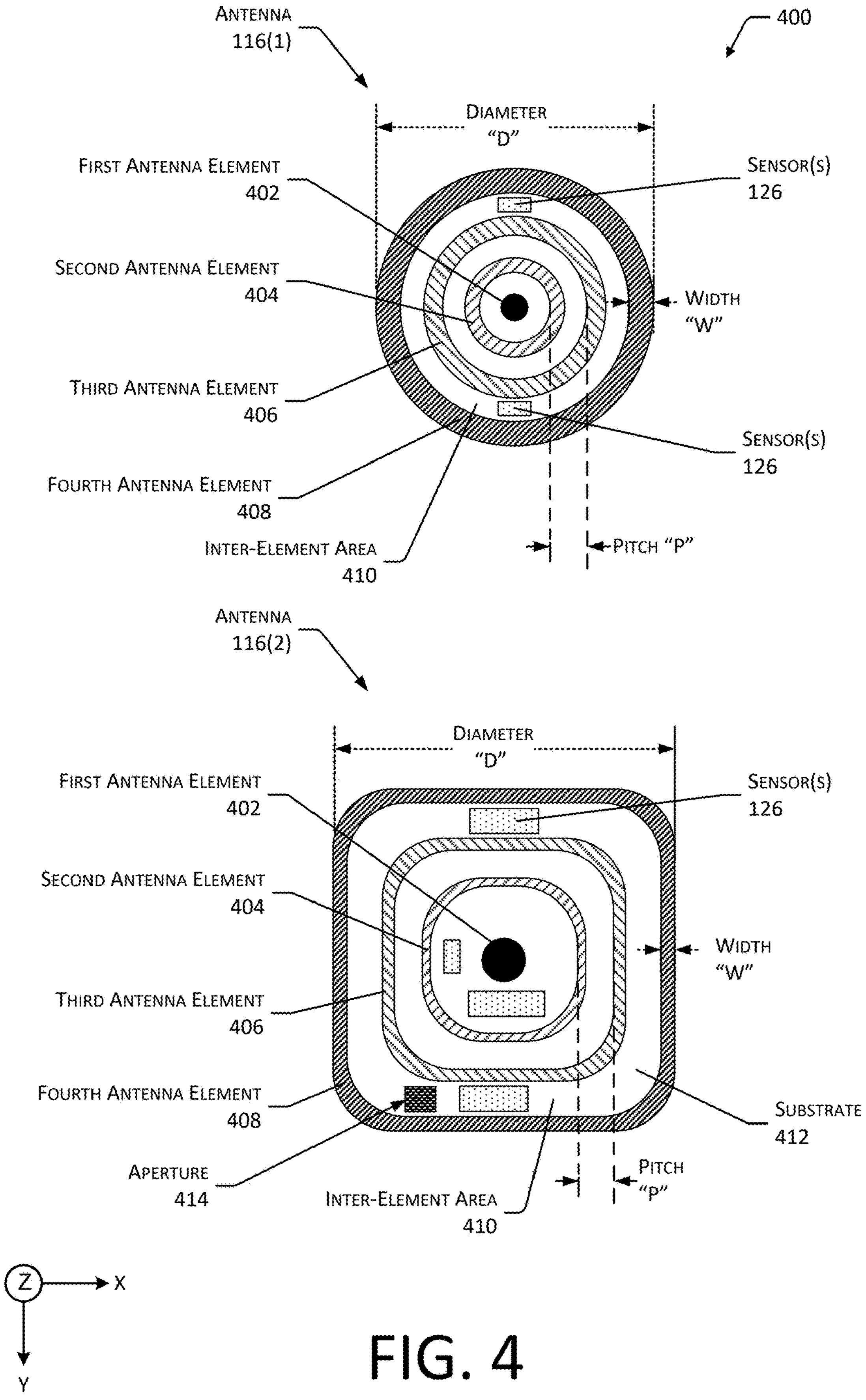
FIG. 4 illustrates one implementation of antenna elements in the antenna.

FIG. 4 illustrates at 400 plan views of some implementations of antenna elements in the antenna 116.

A first implementation of an antenna 116(1) is shown that comprises a first antenna element 402, a second antenna element 404, a third antenna element 406, and a fourth antenna element 408. The second antenna element 404 is arranged around the first antenna element 402. The third antenna element 406 is arranged around the second antenna element 404. The fourth antenna element 408 is arranged around the third antenna element 406. In this implementation, the first antenna element 402 is circular. The other antenna elements 404-408 comprise concentric rings that are centered on the first antenna element 402. In other implementations, one or more of the antenna elements may not be centered with respect to one another. Antenna elements in the antenna 116 may be electrically separated to avoid an electrically conductive path between antenna elements. In some implementations the outermost antenna element may be used as a ground plane during operation of the antenna 116. For example, the fourth antenna element 408 may be used as a ground relative to the first antenna element 402 during operation of the antenna 116.

The antenna 116(1) exhibits a diameter "D" that extends from opposite outside edges of the fourth antenna element 408. Each antenna element has a width "W". In some implementations, the width "W" may vary by antenna element. For example, a width of the second antenna element 404 may be less than a width of the third antenna element 406. Also shown is a pitch "P" between similar features on adjacent antenna elements. For example, the pitch "P" may be measured from an inner edge of adjacent antenna elements.

A second implementation of an antenna 116(2) is shown that comprises a first antenna element 402, a second antenna element 404, a third antenna element 406, and a fourth antenna element 408. The second antenna element 404 is arranged around the first antenna element 402. The third antenna element 406 is arranged around the second antenna element 404. The fourth antenna element 408 is arranged around the third antenna element 406. In this implementation, the first antenna element 402 is circular. The other antenna elements 404-408 are rectangular with rounded corners having a radius of curvature. In some implementations the radius of curvature may be equal to or greater than 1 mm. The antenna elements 404-408 are centered on the first antenna element 402.

An inter-element area 410 is shown between two adjacent antenna elements. For example, there is a first inter-element area 410 between the first antenna element 402 and the second antenna element 404, a second inter-element area 410 between the second antenna element 404 and the third antenna element 406, and a third inter-element area 410 between the third antenna element 406 and the fourth antenna element 408.

The antenna 116 may include a substrate 412 that is electrically non-conductive. For example, the substrate 412 may comprise an insulator such as plastic or glass. The antenna elements may be on, affixed to, incorporated within, or otherwise maintained by the substrate 412. The substrate 412 may be rigid or flexible. For example, the substrate 412 may comprise a plastic layer upon which the antenna elements have been deposited. In one implementation the antenna 116 may comprise a flexible printed circuit with the antenna elements comprising traces thereon.

One or more apertures 414 or sensors 126 may be located within the inter-element area 410 of the antenna 116. The aperture 414 may provide a window or opening in the substrate 412 to facilitate operation of the wearable device 104. For example, the aperture 414 may provide a window through which an optical sensor such as a light emitting diode (LED) or a camera 126(8) is able to operate and acquire data about the user 102. In another example, the aperture 414 may be used by another sensor 126, such as a capacitive sensor, pressure sensor 126(2), and so forth. Some devices may be mounted to the substrate 412 or may be located between the antenna 116 and the user 102 during operation. For example, an LED may be affixed to the substrate 412 and when operated may illuminate a portion of the user 102 that is proximate to the inner surface of the wearable device 104. In some implementations sensors may operate through the substrate 412. For example, if the substrate 412 is flexible a pressure sensor 126(2) may operate through the substrate 412. In another example, the substrate may be transmissive to a signal being detected, such as a particular frequency of light.

The antenna 116 may comprise two or more antenna elements. While four antenna elements are depicted here, in other implementations the antenna 116 may include more or fewer antenna elements. In some implementations arrays of antennas 116 may be used. The arrays may include antennas 112 with different dimensions. For example, a first antenna 116(4) may have a maximum outermost diameter of 10 mm while a second antenna 116(5) has a maximum outermost diameter of 5 mm. One implementation of the antenna array is discussed with regard to FIG. 7.

One or more of the antenna elements may include three or more corners with a radius of curvature equal to or greater than one millimeter. For example, antenna elements 404-408 may each have a rounded triangular shape, a rounded hexagon, and so forth.

The diameter D may be determined based on the sample depth desired during operation. For example, if the first antenna element 402 is used to emit the signal 110, the signal 110 may penetrate the portion of the user 102 that is proximate to the antenna 116 to a depth that is approximately equal to the diameter of the antenna element used to acquire the signal 110. In one implementation the outermost antenna element may have a diameter of 10 mm.

One or more of the antenna elements may comprise closed loops as shown here. For example, the first antenna element 402 may comprise a circular area while the second antenna element 404 comprises an electrically conductive ring. In other implementations, the antenna element 402 may have at least one gap or electrically non-conductive region to form a split ring.

Figure 5:
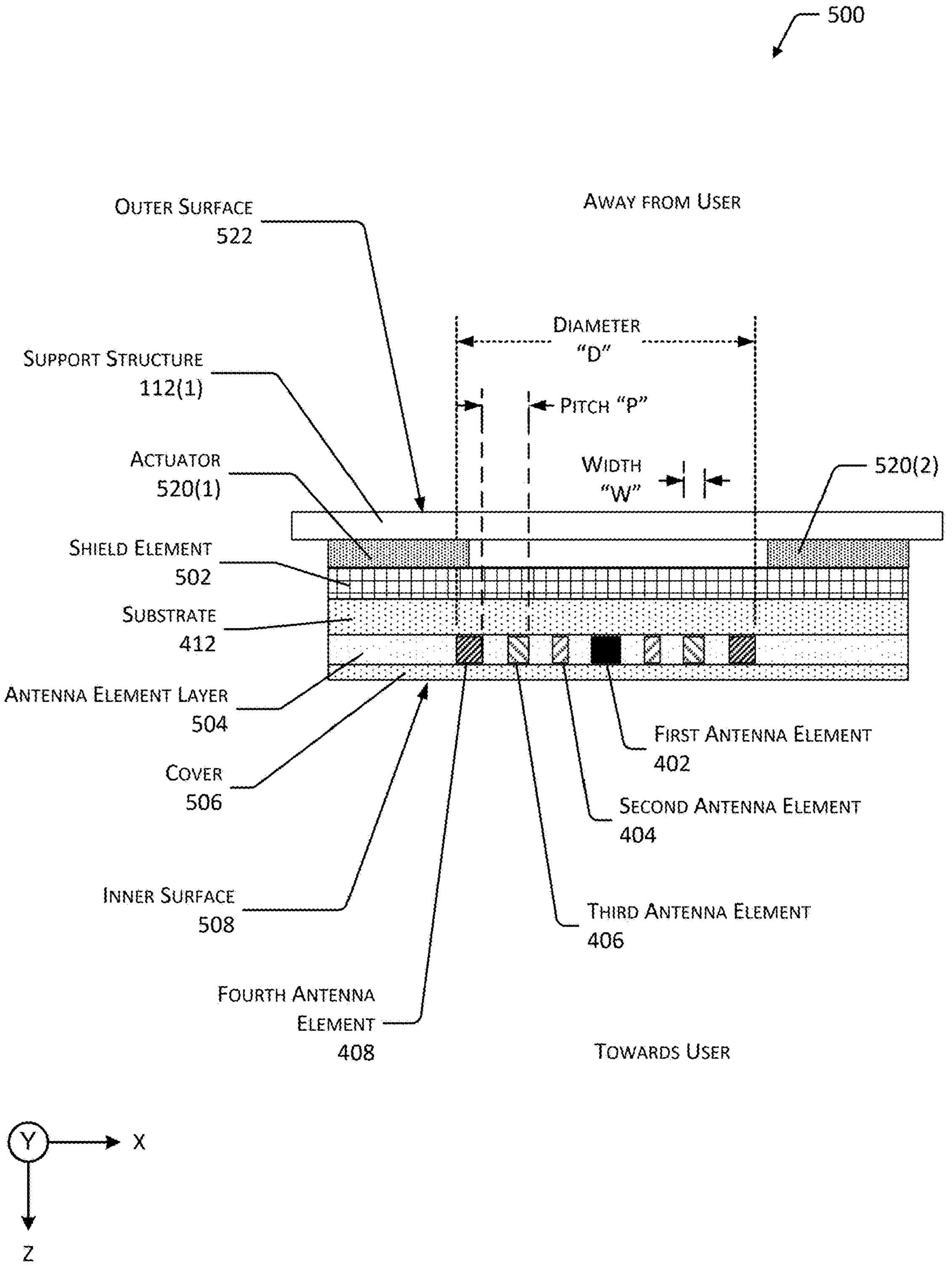
FIG. 5 illustrates a cross section of the antenna as shown in FIG. 4, according to one implementation.

FIG. 5 illustrates a cross section 500 of the antenna 116(1), according to one implementation. As described with regard to FIG. 4, the antenna 116(1) comprises the first antenna element 402, the second antenna element 404, the third antenna element 406, and the fourth antenna element 408 that are supported by the substrate 412. In some implementations, the system may include a shield element 502 or shield that is located behind the substrate 412, on a side opposite where the user 102 will be during use. For example, the shield element 502 may comprise a sheet of electrically conductive material.

The antenna elements may be located in a common plane, which may be designated as an antenna element layer 504. In other implementations, one or more of the antenna elements may be positioned at different heights or have different thicknesses with respect to the substrate 412.

A cover 506 may be used that is adjacent to the antenna elements and is between the antenna elements and the user 102. The cover 506 may comprise a non-conductive material. For example, the cover 506 may comprise plastic, glass, or another material that is transparent to the signal(s) 110. In some implementations the cover 506 may be omitted. In this implementation, the antenna elements may come into direct contact with the skin of the user 102. The antenna elements may comprise a biocompatible material such as gold, silver, rhodium, and so forth. In some implementations the antenna elements may comprise an optically transparent material that is electrically conductive. For example, one or more antenna elements may comprise indium tin oxide. In some implementations, other sensors 126, such as the PPGs 126(1) may operate through the optically transparent and electrically conductive material.

In addition to being used to emit and acquire the signal 110, in implementations where the antenna elements are in contact with the user 102, they may be used to acquire other information. For example, galvanic skin conductivity may be measured using two or more antenna elements, cardiac electrical signals may be acquired using one or more of the antenna elements, and so forth.

An inner surface 508 of the antenna 116(1) is proximate to a portion of the user 102 while the wearable device 104 is being worn.

In some implementations, the sensor device 104 may include one or more actuators 520. In this implementation, the actuators 520 are disposed between the support structure 112(1) and other elements of the sensor device 104, such as the substrate 412. The actuators 520 may be operated to displace at least a portion of the sensor device 104 with respect to the user 102. The actuators 520 may comprise piezoelectric devices, pneumatic devices, fluidic devices, electroactive polymers, motors, and so forth. In the implementation depicted here, the actuators 520 may provide a relative displacement between the substrate 412, an attached antenna element layer 504, and the support structure 112(1). In other implementations the actuators 520 may be positioned on the side of the sensor device 104 that is towards the user 102. During operation, the actuators 520 may be operated to maintain a desired orientation of the antenna element layer 504 with respect to the user 102.

Figure 6:
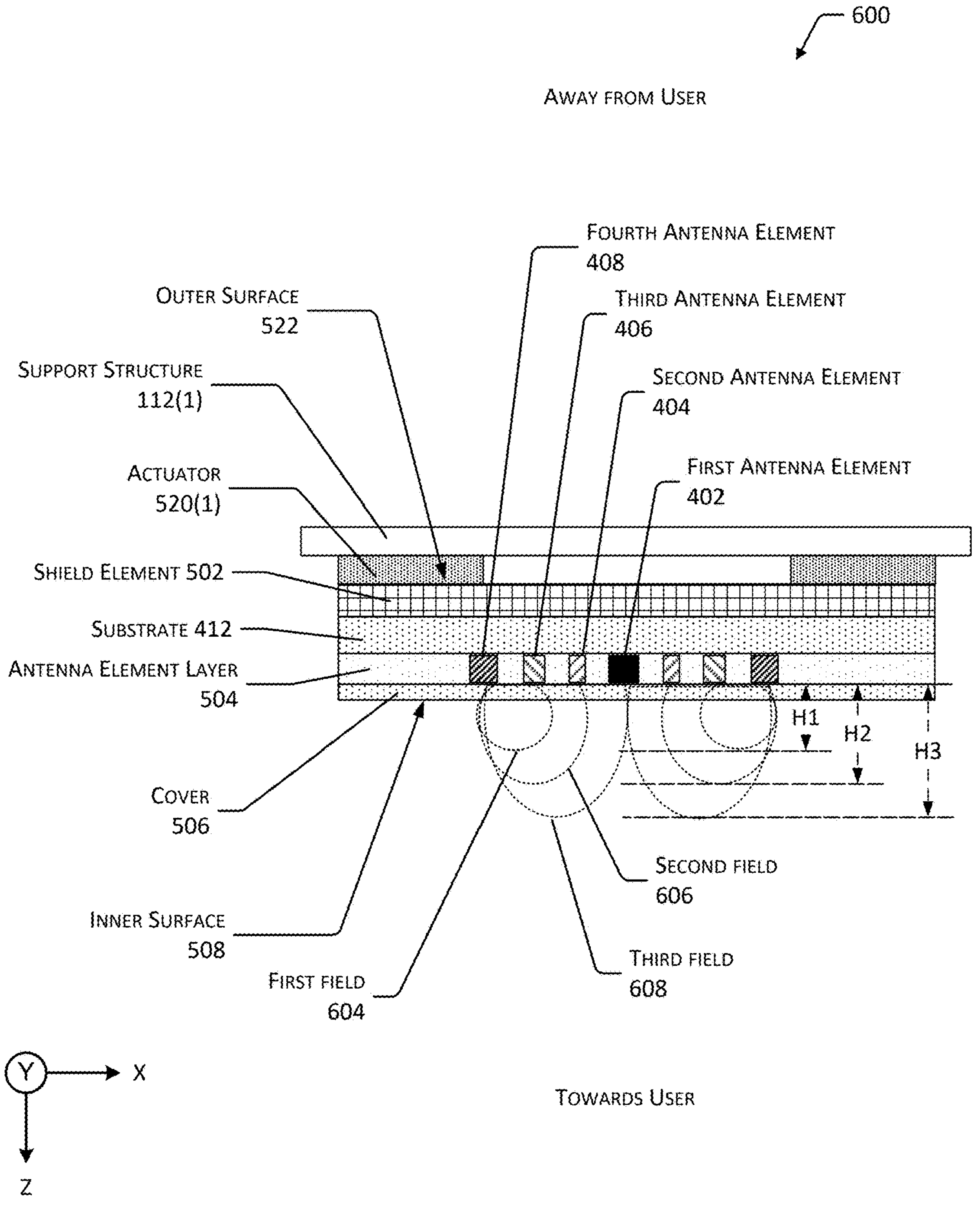
FIG. 6 illustrates the cross section of the antenna as shown in FIG. 5 illustrating emitted RF fields, according to one implementation.

FIG. 6 illustrates a cross section 600 of the antenna 116 as shown in FIG. 5 illustrating emitted RF fields, according to one implementation. As described with regard to FIG. 4, the antenna 116 comprises the first antenna element 402, the second antenna element 404, the third antenna element 406, and the fourth antenna element 408 used as a ground element that are supported by the substrate 412. In some implementations, the system 100 may include a shield element 502 that is located behind the substrate 412 (not shown here), on a side opposite where the user 102 will be during use. For example, the shield element 502 may comprise a sheet of electrically conductive material.

Also depicted, by way of illustration and not as a limitation, are corresponding electrical fields that would extend from the combination of various sets of antenna elements, as switched by the switching circuitry 118 during operation. A first field 604 corresponding to use of the third antenna element 406 and the fourth antenna element 408 is shown that extends a first height H1 from the antenna 116. A second field 606 corresponding to use of the second antenna element 404 and the fourth antenna element 408 is shown that extends a second height H2 from the antenna 116. The second height H2 is greater than the first height H1. A third field 608 corresponding to use of the first antenna element 402 and the fourth antenna element 408 is shown that extends a third height H3 from the antenna 116. The third height H3 is greater than the second height H2. By selecting different sets of antenna elements to use, different distances may be selected, allowing for measurement at different depths within the user 102.

During wear, the support structure 112(2) maintains an inner surface 508 of the antenna 116 proximate to a portion of the user 102 while the sensor device 104 is being worn. An outer surface 522 of the antenna 116 is opposite, away from the user 102.

Figure 7:
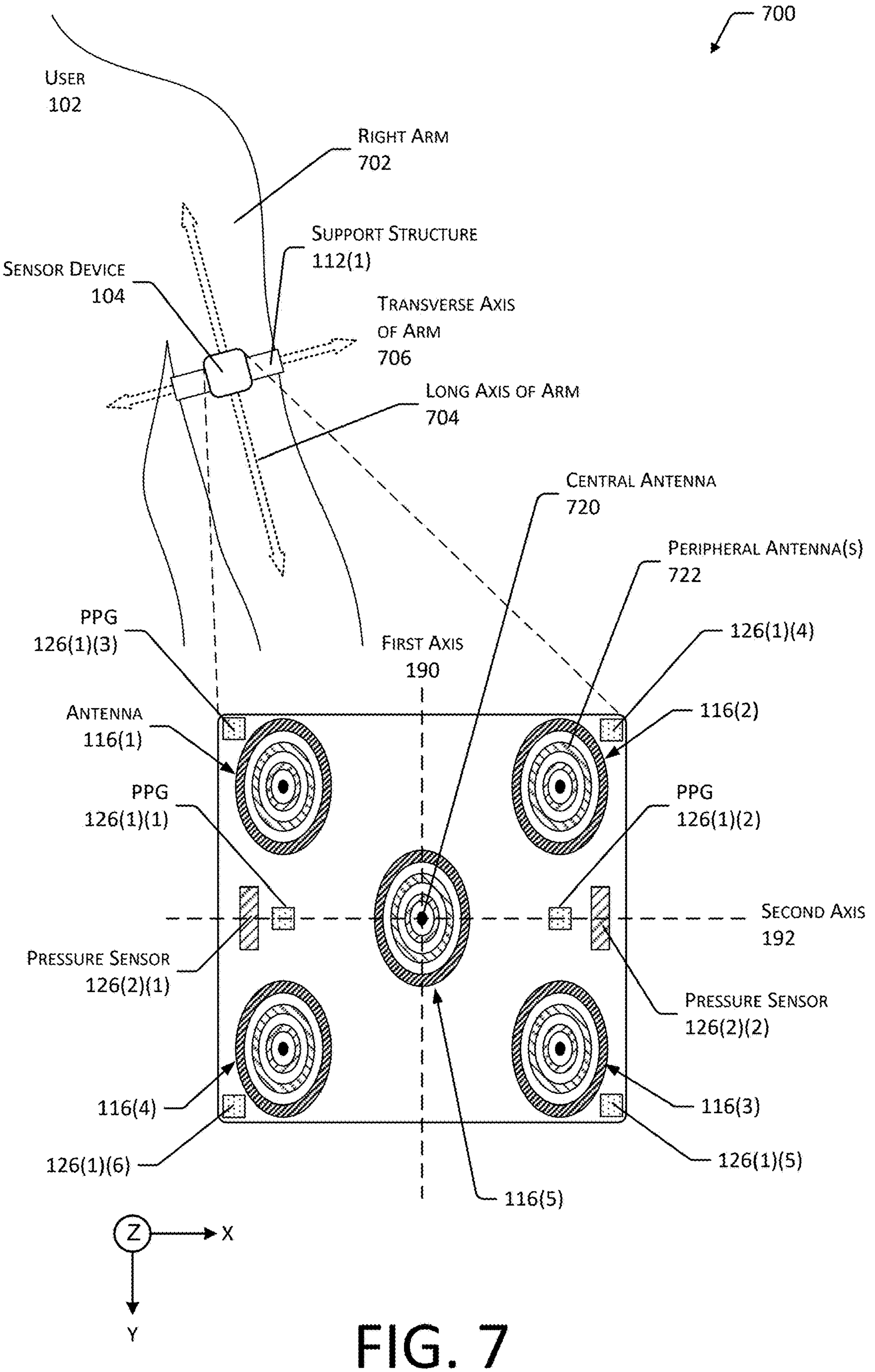
FIG. 7 illustrates placement of a sensor device that comprises an antenna array, according to one implementation.

FIG. 7 illustrates at 700 placement of the sensor device 104 that comprises an antenna array, according to one implementation. A portion of the user 102 is shown, including a right arm 702. The sensor device 104 on the posterior portion of the upper arm, between the shoulder and the elbow, is held in place using the support structure 112(1). In other implementations the sensor device 104 may be placed elsewhere. For example, on the forearm, thigh, calf, abdomen, head, torso, and so forth.

Also shown is a long axis of the arm 704 and a transverse axis of the arm 706 that is perpendicular to the long axis of the arm 704.

An enlarged plan view of the antenna array is shown, with the first axis 190 and the second axis 192. The antennas 116 are arranged in an "X" or quincunx pattern, with a central antenna 720 surrounded by peripheral antennas 722. The central antenna 720 may be proximate to an intersection of the first axis 190 and the second axis 192. For example, the central antenna 720 may be antenna 116(5) while the peripheral antennas 722 comprise antennas 116(1)-(4). The antennas 116 depicted comprise four antenna elements, as described with regard to FIG. 4. In other implementations other configurations of antenna elements may be used. For example, the antennas 116 may comprise two elements: a single element to emit the signal and a surrounding element to act as a ground plane relative to the single element.

During use, the first axis 190 of the antenna array may be parallel to the long axis of the arm 704. In the implementation shown, the antennas 116 have an elongated shape, forming ellipses. The long axes of these ellipses are also parallel to the first axis 190, and also parallel to the long axis of the arm 704.

In this implementation two PPGs 126(1)(1) and 126(1)(2) are shown within the antenna array. The first PPG 126(1)(1) is to one side of the first axis 190 and the second PPG 126(1)(2) is to the other side of the first axis 190. In other implementations other quantities of PPGs 126(1) may be used. For example, the sensor device 104 may comprise a single PPG 126(1).

In this illustration the PPGs 126(1)(1) and 126(1)(2) are each centered on the second axis 192. In other implementations the PPGs 126(1) may be placed elsewhere. These PPGs 126(1) may be used instead of, or in addition to, the PPGS 126(1)(1) and 126(1)(2). For example, PPGs 126(1)(3) through 126(1)(6) may be located at the corners of the sensor device 104. In other implementations, the sensor device 104 may include a larger array of PPGs 126(1), such as 64 PPGs 126(1) arranged in an eight-by-eight array. In other implementations, instead of or in addition to one or more PPGs 126(1), one or more other sensors 126 may be used. For example, one or more optical proximity sensors 126(4) may be used instead of or in addition to the one or more PPGs 126(1) to compensate for motion or relative placement such as tilt of the sensor device 104.

In some implementations, one or more of the elements of the antennas 116 may be optically transparent and electrically conductive, and the PPG 126(1) may be located behind the element, "looking through" the optically transparent material towards the user 102. In other implementations, the PPG 126(1) may be located in the inter-element area 410.

Also shown are pressure sensors 126(2)(1) and 126(2)(2). The pressure sensors 126(2) may be discrete, as shown here, or may comprise a pressure sensitive or pressure detecting array. In the implementation shown, the first pressure sensor 126(2)(1) is to one side of the first axis 190 and the second pressure sensor 126(2)(2) is to the other side of the first axis 190. In other implementations, other arrangements of pressure sensors 126(2) may be used.

Figure 8:
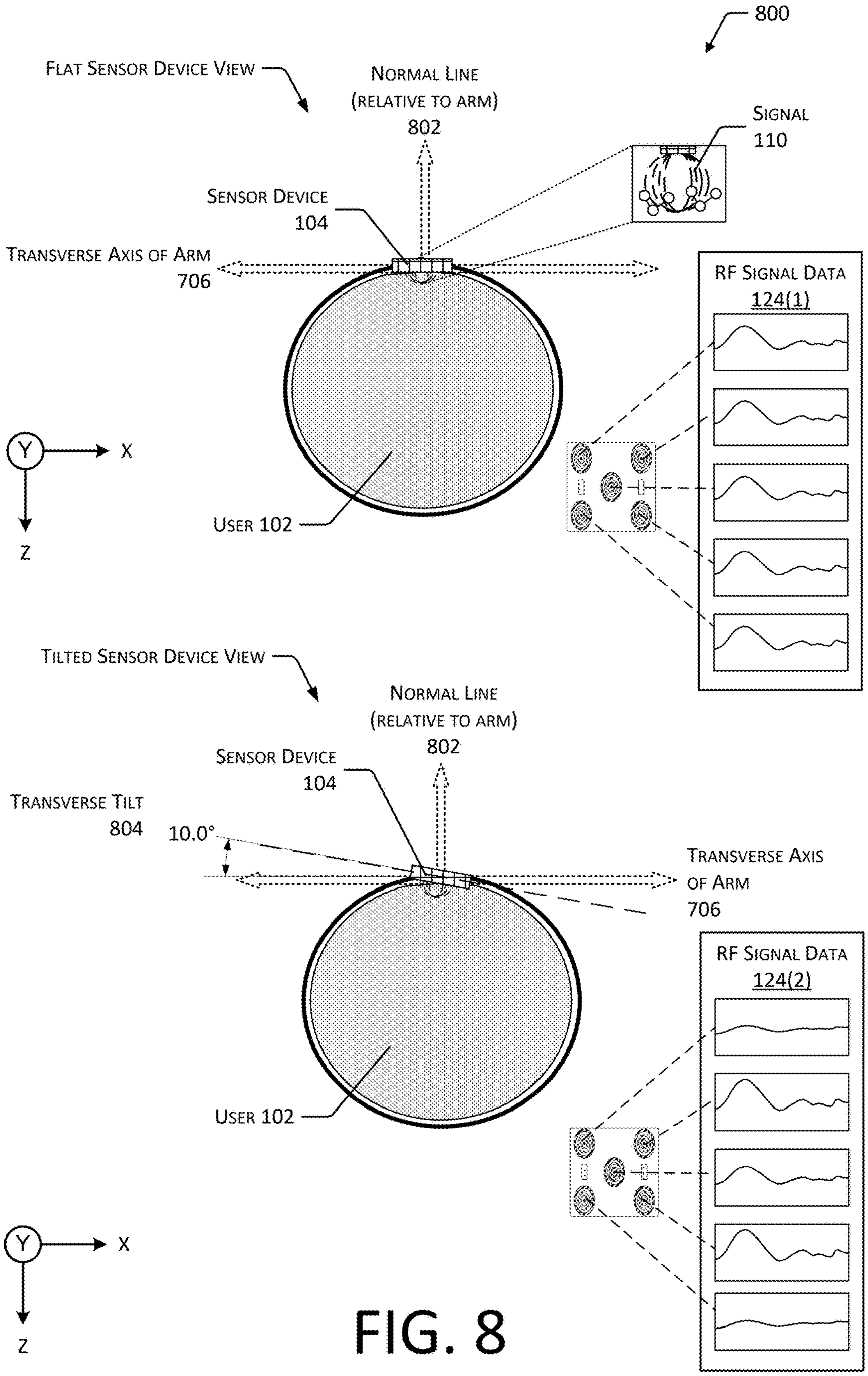
FIG. 8 illustrates the sensor device flat against the arm and with a transverse tilt, according to one implementation.

FIG. 8 illustrates at 800 the sensor device 104 flat against the arm and with a transverse tilt, according to one implementation. In this illustration, a cross section of the upper arm of the user 102 is shown. Also shown is the transverse axis of the arm 706 that is depicted as a line tangent to the posterior surface of the upper arm. Also shown is a normal line 802, that is normal or orthogonal relative to the plane specified by the long axis of the arm 704 (not visible) and the transverse axis of the arm 706.

In the flat sensor device view, the sensor device 104 is arranged, relative to the arm of the user 102, such that there is no tilt relative to the transverse axis of the arm 706. The antenna array is also depicted, with corresponding waveforms of RF signal data 124(1) corresponding to the respective antennas 116(1)-(5). As depicted, the approximate amplitude of the RF signal data 124 acquired using the respective antennas 116 is approximately the same. In this configuration, the RF signal data 124(1) is suitable for determination of concentration data 164.

In comparison, the tilted sensor device view shows the sensor device 104 with a transverse tilt 804. In this example, the transverse tilt 804 of 10 degrees is shown by way of illustration. The antenna array is also depicted, with corresponding waveforms of RF signal data 124(2) corresponding to the respective antennas 116(1)-(5). By comparing RF signal data 124(1) with RF signal data 124(2) as shown in this illustration, the effect of the tilt on the Rf signal data 124 is apparent. The RF signal data 124(2) from antennas 116(1) and 116(4) that are tilted up and away from the arm of the user 102 exhibit a significant decrease in amplitude relative to the RF signal data 124(2) from antenna 116(5) in the center, and the other antennas 116. Continuing the example, antennas 116(2) and 116(3) are tilted down and press in the arm of the user 102 and may exhibit an increased amplitude as shown here.

In implementations in which the sensor device 104 includes one or more actuators 520, the actuators 520 may be operated to attempt to return the sensor device 104 to the desired orientation with respect to the user 102. For example, the actuator 520(1) on the left side of the sensor device 104 in this illustration may be activated in an attempt to push the left side of the sensor device 104 closer to the user 102.

This illustration shows only a moment in time. Without use of the compensation module 154, the various changes in amplitude or other characteristics of the RF signal data 124 due to movement would result in poor quality concentration data 164, if at all.

Figure 9:
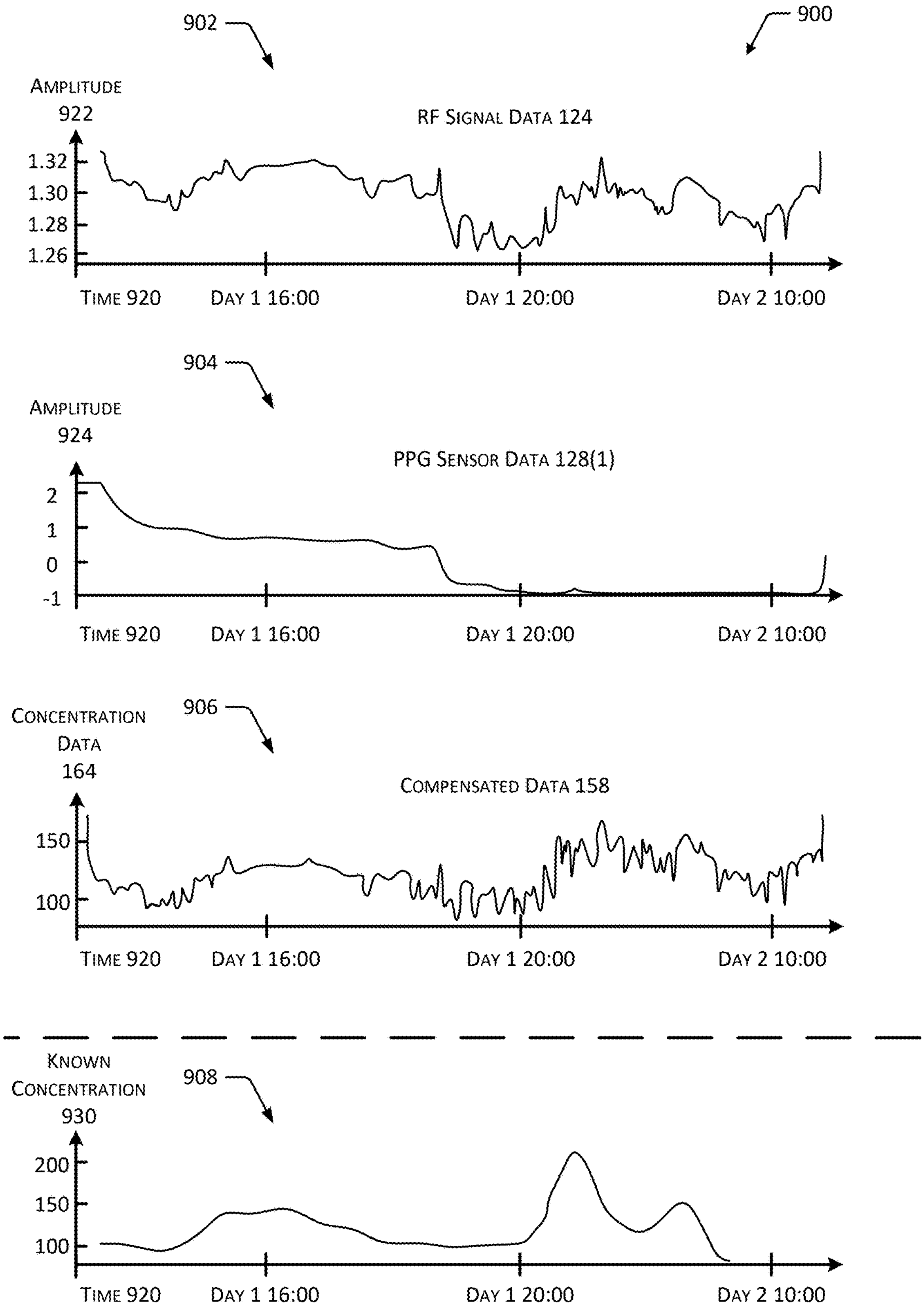
FIG. 9 illustrates graphs of RF signal data, sensor data, compensated data, and a known signal, according to one implementation.

FIG. 9 illustrates at 900 graphs of PPG sensor data 128(1), RF signal data 124, compensated data 158, and a known signal, according to one implementation.

In this set of graphs 902-908, time 920 is depicted along the horizontal axis spanning two days. Graph 902 depicts, relative to time 920, the amplitude 922 of the RF signal data 124 as acquired. This may comprise RF signal data 124 from a single antenna 116, a composite of RF signal data 124 from the antenna array, and so forth. The RF signal data 124 in this illustration may be representative of impedance of the antenna 116, as measured at that time. Each measurement shown may comprise a plurality of individual samples, that may have had other processing such as averaging fifty samples to determine one measurement or datapoint on this graph 902. The amplitude 922 may be the amplitude of a voltage of the RF circuitry 114 that is representative of the impedance of the antenna 116 at that time.

Graph 904 depicts, relative to the time 920, the amplitude 924 of PPG sensor data 128(1) from one or more PPGs 126(1). Each measurement shown may comprise a plurality of individual samples, that may have had other processing such as averaging ten samples to determine one measurement or datapoint on this graph 904. Note that between 16:00 and 20:00 on day 1, the overall amplitude of the signal dropped. Such changes in amplitude may be representative of movement of the sensor device 104 relative to the user 102. For example, at that time the user 102 may have bumped or pushed the sensor device 104 into a different position with respect to their arm.

Graph 906 depicts, relative to the time 920, the compensated data 158 produced by the compensation module 154 using the PPG sensor data 128(1) to determine the compensation values 156 as discussed above to process the RF signal data 124. One implementation may be visualized as subtracting the PPG sensor data 128 graph from the RF signal data 124 graph.

The resulting compensated data 158 may then be used by the data processing module 160 to determine the concentration data 164.

Graph 908 depicts known concentrations 930, relative to the time 920, such as provided by an invasive glucose monitoring system. Graphs 906 and 908 show a clear correspondence, with the compensated data 158 having an overall curve that is consistent with the known concentration 630. This correspondence is a substantial improvement when the RF signal data 124 shown in graph 902 is compared to the known concentrations 930 of graph 908.

Figure 10:
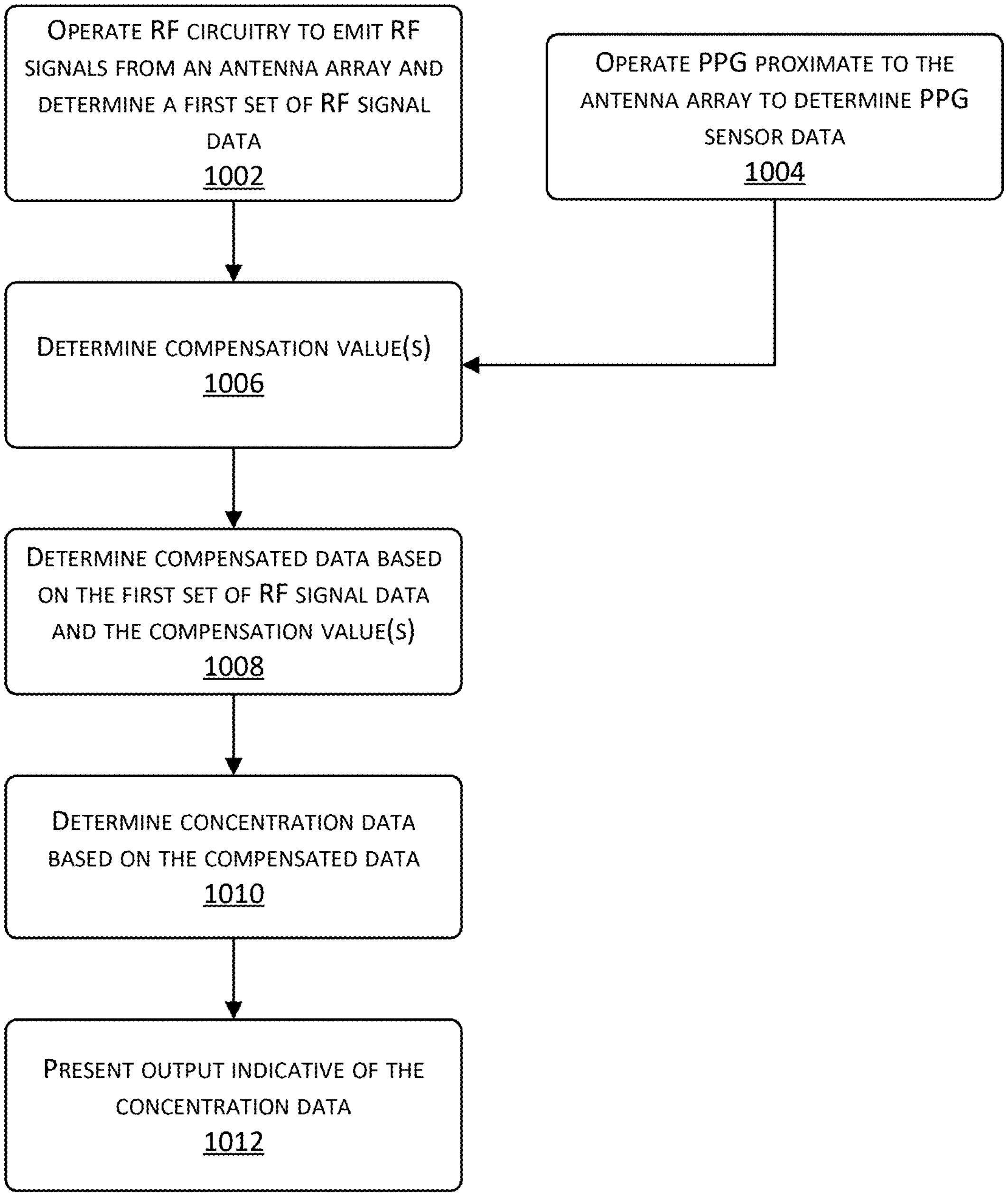
FIG. 10 illustrates a flow diagram of a process of using radio frequency signals emitted by the antenna array to determine molecular concentration data, according to one implementation.

FIG. 10 illustrates at 1000 a flow diagram of a process of using radio frequency signals 110 emitted by the antenna array to determine molecular concentration data 164, according to one implementation. The process may be implemented at least in part by one or more of the sensor device 104, the wearable device 106, or the other device 180.

At 1002, the RF circuitry 114 is operated to emit RF signals 110 from an antenna array and determine a first set of RF signal data 124. The RF signal data 124 may comprise data indicative of one or more measurements of one or more characteristics of the RF circuitry 114 or a portion thereof during operation. The RF signal data 124 may comprise a time series of measurements. Individual measurements may be obtained from individual antennas 116 in the antenna array, or elements thereof.

At 1004 a sensor 126 proximate to the antenna array is operated to determine sensor data 128. In one implementation, a PPG 126(1) may be operated to determine PPG sensor data 128(1). A single PPG 126(1) or a plurality of PPGs 126(1)(N) may be used. For example, PPGs 126(1)(3)-126(1)(6) may be positioned proximate to the corners of the sensor device 104. In other implementations not shown here, other sensors 126 such as pressure sensors 126(2), proximity sensors 126(4), cameras 126(8), and so forth may be used to determine sensor data 128.

At 1006 one or more compensation values 156 are determined. For example, the compensation module 154 may determine the one or more compensation values 156. In one implementation the compensation values 156 may be determined based on the first set of RF signal data 124. For example, the RF signal data 124 from respective antennas 116 in the antenna array may be processed to determine the compensation values 156. In another implementation, the compensation values 156 may be determined based on the sensor data 128, such as the PPG sensor data 128(1).

At 1008 compensated data 158 is determined based on the first set of RF signal data 124 and the compensation values 156. For example, the compensated data 158 may be determined by the compensation module 154. In one implementation, the compensation values 156 may comprise a time series of values that are then subtracted from a time-aligned time series of values in the first set of RF signal data 124.

At 1010 concentration data 164 is determined based on the compensated data 158. For example, the data processing module 160 may use the reference data 162 and the compensated data 158 to determine the concentration data 164. Continuing the example, the concentration data 164 may include glucose level data. In another example, the compensated data 158 may be provided as input to a trained machine learning system which then provides as output the concentration data 164.

At 1012 output indicative of the concentration data 164 is presented. In one implementation, the user interface module 166 may generate output data 168 that is used by the one or more output devices 170 to present output to the user 102. For example, a graphical indication may be provided using a display device 170(3) of the other device 180.

While the system and techniques described herein are used with respect to measure humans, it is understood that these techniques may be used to monitor other types of animals. In some implementations, the systems and techniques may be used to characterize other objects. For example, the system may be used to determine a sugar concentration in a fruit, water concentration in a mixture, and so forth.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A system comprising:

an antenna array comprising a central antenna and a set of peripheral antennas;

a support structure that retains the antenna array proximate to a user;

radio frequency (RF) circuitry coupled to the antenna array;

a memory, storing computer-executable instructions; and one or more hardware processors that execute the computer-executable instructions to:

operate the RF circuitry to determine first signal data associated with the central antenna;

operate the RF circuitry to determine a first set of signal data, wherein each signal of the first set of signal data is associated with a respective antenna of the set of peripheral antennas;

determine one or more compensation values based on a comparison of the first signal data and the first set of signal data; and determine, based on the first signal data, the first set of signal data, and the one or more compensation values, compensated data.

2. The system of claim 1, wherein:

the antenna array has a first axis and a second axis orthogonal to the first axis, the first axis is parallel to a long axis of a limb of the user, and the set of peripheral antennas comprises:

a first antenna at a first location on a first side with respect to the first axis and the second axis;

a second antenna at a second location that is on a second side with respect to the first axis and the first side with respect to the second axis;

a third antenna at a third location that is on the second side with respect to the first axis and a second side with respect to the second axis;

a fourth antenna at a fourth location that is on the first side with respect to the first axis and the second side with respect to the second axis; and the central antenna is proximate to an intersection of the first axis and the second axis.

3. The system of claim 1, further comprising at least one photoplethysmograph (PPG) that is located proximate to or within the antenna array; and the one or more hardware processors further execute the computer-executable instructions to:

determine PPG sensor data using the at least one PPG; and wherein the one or more compensation values are further based on the PPG sensor data.

4. The system of claim 3, wherein at least a portion of the antenna array comprises an optically transparent material that is electrically conductive; and wherein the at least one PPG one or more of emits light to the user or detects reflected light from the user through at least a portion of the optically transparent material.

5. The system of claim 1, wherein each antenna of the antenna array comprises a respective electrically conductive element and ground plane.

6. The system of claim 1, wherein:

the antenna array has a first axis and a second axis orthogonal to the first axis;

the first axis is parallel to a long axis of a limb of the user;

a first PPG is at a first location on a first side of the antenna array with respect to the first axis; and a second PPG is at a second location on a second side of the antenna array with respect to the first axis; and the one or more hardware processors further execute the computer-executable instructions to:

determine PPG sensor data using the first PPG and the second PPG; and wherein the one or more compensation values are further based on the PPG sensor data.

7. The system of claim 1, the one or more hardware processors further execute the computer-executable instructions to:

determine, based on the compensated data, concentration data indicative of a concentration of a type of molecule within the user.

8. The system of claim 1, further comprising:

a pressure sensor proximate to the antenna array; and the one or more hardware processors further execute the computer-executable instructions to:

operate the pressure sensor to determine pressure data; and determine the one or more compensation values based at least in part on the pressure data.

9. A system comprising:

an antenna array comprising a plurality of antennas;

a support structure that retains the antenna array proximate to a user;

radio frequency (RF) circuitry coupled to the antenna array;

a first photoplethysmograph (PPG) that is proximate to the antenna array;

a memory, storing computer-executable instructions; and one or more hardware processors that execute the computer-executable instructions to:

operate the RF circuitry to determine RF signal data;

determine PPG sensor data using the first PPG:

determine one or more compensation values based on the RF signal data and the PPG sensor data; and determine compensated data based on the RF signal data and the one or more compensation values.

10. The system of claim 9, wherein:

the antenna array has a first axis and a second axis orthogonal to the first axis, the first axis is parallel to a long axis of a limb of the user, and the antenna array comprises:

a first antenna at a first location on a first side with respect to the first axis and the second axis;

a second antenna at a second location that is on a second side with respect to the first axis and the first side with respect to the second axis;

a third antenna at a third location that is on the second side with respect to the first axis and a second side with respect to the second axis;

a fourth antenna at a fourth location that is on the first side with respect to the first axis and the second side with respect to the second axis; and a fifth antenna proximate to an intersection of the first axis and the second axis.

11. The system of claim 9, wherein each antenna of the plurality of antennas comprises a respective element and ground plane.

12. The system of claim 9, wherein:

the antenna array has a first axis and a second axis orthogonal to the first axis, the first axis is parallel to a long axis of a limb of the user, the first PPG is at a first location on a first side with respect to the first axis, a second PPG is at a second location on a second side with respect to the first axis, and the PPG sensor data is determined using the first PPG and the second PPG.

13. The system of claim 9, wherein at least one of the plurality of antennas comprises an optically transparent material that is electrically conductive; and wherein the first PPG one or more of emits light to the user or detects reflected light from the user through at least a portion of the optically transparent material.

14. The system of claim 9, further comprising:

a first housing that retains the antenna array and the first PPG;

wherein the support structure retains the first housing proximate to the user;

a second housing that retains at least a portion of the RF circuitry, the memory, and the one or more hardware processors;

a first set of one or more electrical conductors that connect the antenna array to the RF circuitry; and a second set of one or more electrical conductors that connect the first PPG to the one or more hardware processors.

15. The system of claim 9, the one or more hardware processors to further execute the computer-executable instructions to:

determine, based on the compensated data, concentration data indicative of a concentration of a type of molecule within the user.

16. The system of claim 9, further comprising:

a pressure sensor proximate to the antenna array; and the one or more hardware processors to further execute the computer-executable instructions to:

operate the pressure sensor to determine pressure data; and wherein the compensated data is further based on the pressure data.

17. A method comprising:

operating radio frequency (RF) circuitry comprising an antenna array to determine a first set of signal data, wherein each signal represented by the first set of signal data is associated with a respective antenna of the antenna array;

operating a pressure sensor that is proximate to the antenna array to determine pressure sensor data;

determining, based on the first set of signal data and the pressure sensor data, one or more compensation values; and determining, based on the first set of signal data and the one or more compensation values, compensated data.

18. The method of claim 17, further comprising:

operating a photoplethysmograph (PPG) that is proximate to the antenna array to determine PPG sensor data; and wherein the determining the one or more compensation values is further based on the PPG sensor data.

19. The method of claim 17, further comprising:

determining, based on the compensated data, concentration data indicative of a concentration of a type of molecule within a user.

20. The method of claim 17, further comprising:

operating a first photoplethysmograph (PPG) and a second PPG that are both proximate to the antenna array to determine PPG sensor data;

wherein the determining the one or more compensation values is further based on the PPG sensor data.

* * * * *